United States Patent
McComas et al.

(10) Patent No.: US 7,297,713 B2
(45) Date of Patent: Nov. 20, 2007

(54) CYANOPYRROLE-PHENYL AMIDE PROGESTERONE RECEPTOR MODULATORS AND USES THEREOF

(75) Inventors: Casey Cameron McComas, Phoenixville, PA (US); Andrew Fensome, Wayne, PA (US); Edward George Melenski, Collegeville, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/494,069

(22) Filed: Jul. 27, 2006

(65) Prior Publication Data

US 2007/0027125 A1 Feb. 1, 2007

Related U.S. Application Data

(60) Provisional application No. 60/704,008, filed on Jul. 29, 2005.

(51) Int. Cl.
*A61K 31/40* (2006.01)
*C07D 207/34* (2006.01)

(52) U.S. Cl. ..................... 514/427; 548/561
(58) Field of Classification Search ............... 514/427; 548/561
See application file for complete search history.

(56) References Cited

U.S. PATENT DOCUMENTS

| | | | |
|---|---|---|---|
| 3,270,029 | A | 8/1966 | Palazzo |
| 4,680,413 | A | 7/1987 | Genda et al. |
| 4,857,651 | A | 8/1989 | Brown et al. |
| 4,929,634 | A | 5/1990 | Herman et al. |
| 4,968,683 | A | 11/1990 | Mörsdorf et al. |
| 5,210,092 | A | 5/1993 | Oku et al. |
| 5,215,994 | A | 6/1993 | Oku et al. |
| 5,223,498 | A | 6/1993 | Gopalan |
| 5,284,863 | A | 2/1994 | Barnes et al. |
| 5,302,720 | A | 4/1994 | Gopalan |
| 5,310,938 | A | 5/1994 | Brown et al. |
| 5,328,928 | A | 7/1994 | Addor et al. |
| 5,354,759 | A | 10/1994 | Oku et al. |
| 5,449,789 | A | 9/1995 | Kameswaran |
| 5,455,263 | A | 10/1995 | Doscher |
| 5,518,891 | A | 5/1996 | Gibboni et al. |
| 5,563,279 | A | 10/1996 | Kameswaran |
| 5,597,825 | A | 1/1997 | Himmelsbach et al. |
| 5,847,006 | A | 12/1998 | Magar et al. |
| 5,902,824 | A | 5/1999 | Ulrich |
| 5,932,520 | A | 8/1999 | Van der Flass et al. |
| 5,939,556 | A | 8/1999 | Zoller et al. |
| 5,952,362 | A | 9/1999 | Cournoyer et al. |
| 6,057,349 | A | 5/2000 | Cournoyer et al. |
| 6,242,613 | B1 | 6/2001 | Schaaf et al. |
| 6,414,005 | B1 | 7/2002 | Makino |
| 6,417,372 | B2 | 7/2002 | Schaaf et al. |
| 6,664,395 | B2 | 12/2003 | Letavic et al. |
| 2001/0020100 | A1 | 9/2001 | Manning et al. |
| 2001/0047023 | A1 | 11/2001 | Shrikhande et al. |
| 2004/0138287 | A1 | 7/2004 | Barth et al. |
| 2005/0239779 | A1* | 10/2005 | Wilk ........................ 514/230.5 |
| 2006/0034786 | A1 | 2/2006 | Michelet et al. |

FOREIGN PATENT DOCUMENTS

| | | |
|---|---|---|
| CA | 2055636 | 5/1992 |
| DE | 3601285 | 7/1987 |
| DE | 19918725 | 10/2000 |
| EP | 003640 | 8/1979 |
| EP | 0043659 | 1/1982 |
| EP | 0358047 | 3/1990 |
| EP | 0426948 | 5/1991 |
| EP | 0484614 | 5/1992 |
| EP | 0491136 | 6/1992 |
| EP | 0549866 | 7/1993 |
| EP | 553682 | 8/1993 |
| EP | 0600157 | 6/1994 |

(Continued)

OTHER PUBLICATIONS

Brown et al., "Aryl-Pyrrole as Insecticide, Acaricide and Nematocide, and its Production", English Abstract of Japanese Patent No. JP-04-095068.
Kamiyama et al., "Analysis and Reagent and Analytical Element Used Therfor", English Abstract of Japanese Patent No. JP-03-254699.
Gopalan, "Therapeutic Agents", English Abstract of Chinese Patent No. CN1057648 (Jan. 8, 1992).
Collins et al., "Novel Pyrrole-Containing Progesterone Receptor Modulators" Bioorg. & Med. Chem. Lett., 14:2185-2189 (May 3, 2004).
Vorob'ev et al., "Convenient Synthesis of 5-Amino-1-Aryltetrazoles", Vestsi Natsyyanal'nai Akademii Navuk Belarusi, Seryya Khimichnykh Naruk 2: 50-53 (2003).

(Continued)

*Primary Examiner*—Rebecca Anderson
*Assistant Examiner*—Michael P. Barker
(74) *Attorney, Agent, or Firm*—Howson & Howson LLP; Arnold S. Milowsky

(57) ABSTRACT

Progesterone receptor modulators of formula I, or a pharmaceutically acceptable salt thereof,

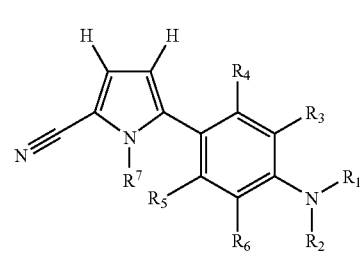

wherein $R_1$, $R_2$, $R_3$, $R_4$, $R_5$, $R_6$, and $R_7$ are as defined herein. These compounds are useful for contraception and hormone replacement therapy. Also provided are products containing these compounds.

18 Claims, No Drawings

FOREIGN PATENT DOCUMENTS

| | | |
|---|---|---|
| EP | 0821876 | 2/1998 |
| EP | 1310492 | 5/2003 |
| GB | 1215858 | 12/1970 |
| WO | WO93/16071 | 8/1993 |
| WO | WO93/19067 | 9/1993 |
| WO | WO94/04153 | 3/1994 |
| WO | WO98/48800 | 11/1998 |
| WO | WO 00/049015 | 8/2000 |
| WO | WO 00/57877 | 10/2000 |
| WO | WO 00/66581 | 11/2000 |
| WO | WO 02/72576 | 9/2002 |
| WO | WO 02/72579 | 9/2002 |
| WO | WO 02/089734 | 11/2002 |
| WO | WO 04/029040 | 4/2004 |
| WO | WO-04/039795 | 5/2004 |
| WO | WO-04/043926 | 5/2004 |
| WO | WO-04/058249 | 7/2004 |
| WO | WO-04/069227 | 8/2004 |
| WO | WO-05/105739 | 11/2005 |
| WO | WO-06/023107 | 3/2006 |
| WO | WO-06/023109 | 3/2006 |
| ZA | 906550 | 6/1991 |

OTHER PUBLICATIONS

Vorob'ev et al., "Convenient Synthesis of 5-Amino-1-Aryltetrazoles", Vestsi Natsyyanal'nai Akademii Navuk Belarusi, Seryya Khimichnykh Naruk 2: 50-53 (2003) - English abstract.

Kamijo et al., "Cyanamide Synthesis by the palladium-Catalyst Cleavage of a Si-N Bond", Angewandte Chemie, International Ed., 41(10):1780-1782 (2002).

Evans et al., "Effect of Conjugation on the Oscillator Strength of the Ruthenium (III)- Cyanamide Chromophore", Inorganic Chemistry, 34(6):1350-4 (1995).

Gaponik et al., "Synthesis and Properties of Phenylenebis-1H-tetrazoles", Khimiya Geterotsiklicheskikh Soedinenii 11:1528-32 (Nov. 1990) - English translation.

Reisz et al., "Two New Direct Monoazo Dyes", Bulletin Scientifique de l'Institut Texteil de France, 11(43):61-3 (1982).

Reisz et al., "Two New Direct Monoazo Dyes", Bulletin Scientifique de l'Institut Texteil de France, 11(43):61-3 (1982) - English abstract.

Pankratov et al., "Synthesis of Aromatic Cyanamides", Bull. Acad. Sci. IKKR Div. Chem. Sci. 24:2198 (1975) - translated from Izv. Akad. Nauk SSSR Ser. Khim. 24(10) :2315-2316 (Oct. 1975).

* cited by examiner

CYANOPYRROLE-PHENYL AMIDE PROGESTERONE RECEPTOR MODULATORS AND USES THEREOF

CROSS-REFERENCE TO RELATED APPLICATIONS

This application claims the benefit of the priority of U.S. Provisional Patent Application No. 60/704,008, filed Jul. 29, 2005.

BACKGROUND OF THE INVENTION

Progesterone receptor (PR) agonists and antagonists, also termed PR modulators, have been described for use in contraception and a variety of other indications.

What are needed are novel PR modulators which are useful as contraceptives.

SUMMARY OF THE INVENTION

In one aspect, PR modulators are provided.

In still another aspect, uses of the compounds described herein are provided for hormone replacement therapy, treatment and/or prevention of uterine myometrial fibroids, endometriosis, benign prostatic hypertrophy, carcinomas and adenocarcinomas of the endometrium, ovary, breast, colon, prostate, pituitary, meningioma and other hormone-dependent tumors, dysmenorrhea, dysfunctional uterine bleeding, cycle-related symptoms, and symptoms of premenstrual syndrome and premenstrual dysphoric disorder, or the synchronization of the estrus in livestock.

In another aspect, pharmaceutical compositions containing a PR modulator described herein, optionally in combination with a progestin or estrogen are provided.

Other aspects and advantages of the present invention are described further in the following detailed description of the preferred embodiments thereof.

DETAILED DESCRIPTION OF THE INVENTION

Compounds useful for hormone replacement therapy, treatment and/or prevention of uterine myometrial fibroids, endometriosis, benign prostatic hypertrophy, carcinomas and adenocarcinomas of the endometrium, ovary, breast, colon, prostate, pituitary, meningioma and other hormone-dependent tumors, dysmenorrheal, dysfunctional uterine bleeding, cycle-related symptoms, and symptoms of premenstrual syndrome and premenstrual dysphoric disorder, or synchronization of estrus in livestock are provided.

A progesterone receptor modulator is thereby characterized by having the structure of formula I:

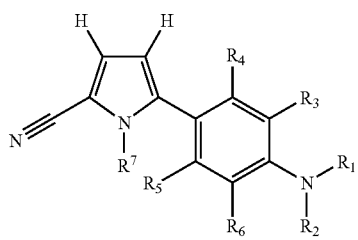

I wherein:
$R_1$ is selected from among:
H,
CN,
C(O)—$C_1$-$C_6$ alkyl, C(O)—$C_3$-$C_8$ cycloalkyl, C(O)-substituted $C_1$-$C_6$ alkyl, C(O)-aryl, C(O)-substituted aryl, C(O)-heteroaryl, C(O)-heterocycle, C(O)—$C_3$-$C_6$ alkenyl, C(O)—$C_3$-$C_6$ alkynyl, C(O)-substituted $C_3$-$C_6$ alkenyl, C(O)-substituted $C_3$-$C_6$ alkynyl,
C(O)O—$C_1$—$C_6$ alkyl, C(O)O—$C_3$-$C_8$ cycloalkyl, C(O)O-substituted $C_1$-$C_6$ alkyl, C(O)O-aryl, C(O)O-substituted aryl, C(O)O-heteroaryl, C(O)O-heterocycle, C(O)O—$C_3$-$C_6$ alkenyl, C(O)O—$C_3$-$C_6$ alkynyl, C(O)O—$C_3$-$C_6$ substituted alkenyl, C(O)O—$C_3$-$C_6$ substituted alkynyl,
C(O)NH—$C_1$-$C_6$ alkyl, C(O)NH—$C_3$-$C_8$ cycloalkyl, C(O)N-di-$C_3$-$C_8$ cycloalkyl, C(O)N-di $C_1$-$C_6$ alkyl, C(O)N-di-substituted $C_1$-$C_6$ alkyl, C(O)NH-substituted $C_1$-$C_6$ alkyl, C(O)NH-aryl, C(O)N-di-aryl, C(O)NH-substituted aryl, C(O)N-di-substituted aryl, C(O)NH-heteroaryl, C(O)N-diheteroaryl, C(O)NH-heterocycle, C(O)N-diheterocycle, C(O)NH—$C_3$-$C_6$ alkenyl, C(O)NH—$C_3$-$C_6$ alkynyl, C(O)NH-substituted $C_3$-$C_6$ alkenyl, C(O)NH-substituted $C_3$-$C_6$ alkynyl, and
$R_1$ is a linking group to a second structure of formula I to form a dimer of formula I, said linking group is a C(O)— group;
$R_2$ is selected from among H, $C_1$-$C_6$ alkyl, substituted $C_1$-$C_6$ alkyl, and $C_3$-$C_6$ cycloalkyl;
provided that $R_1$ and $R_2$ both are not H,
provided that when $R_1$ is C(O) substituted aryl, $R_2$ is not H;
provided that when $R_1$ is H and $R_7$ is H, $R_2$ is not $C_1$-$C_6$ alkyl;
$R_3$, $R_4$, $R_5$ and $R_6$ are independently selected from among H, halogen, $C_1$-$C_6$ alkyl, substituted $C_1$-$C_6$ alkyl, $C_3$-$C_6$ cycloalkyl, O—$C_1$-$C_6$ alkyl, O—$C_1$-$C_6$ substituted alkyl, aryl, heteroaryl, heterocycle, substituted aryl, substituted heteroaryl, and substituted heterocycle;
$R_7$ is selected from among H, $C_1$-$C_6$ alkyl, substituted $C_1$-$C_6$ alkyl, $C_3$-$C_6$ cycloalkyl, and substituted $C_3$-$C_6$ cycloalkyl.

In one embodiment, the compound has the structure of formula I, wherein:
$R_1$ is CN;
$R_2$ is H or $C_1$-$C_6$ alkyl;
$R_3$, $R_4$, $R_5$ and $R_6$ are independently selected from among H, halogen, $C_1$-$C_6$ alkyl, $C_3$-$C_6$ cycloalkyl, O—$C_1$-$C_6$ alkyl, and O—$C_1$-$C_6$ substituted alkyl; and
$R_7$ is H or $C_1$-$C_6$ alkyl.

In another embodiment, the compound has the structure of formula I, wherein:
$R_1$ is CN;
$R_2$ is H,
$R_3$, $R_4$, $R_5$ and $R_6$ are independently selected from H, halogen, $C_1$-$C_6$ alkyl, and O—$C_1$-$C_6$ alkyl; and
$R_7$ is H or $C_1$-$C_6$ alkyl.

In yet another embodiment, the compound has the structure of formula I, wherein:
$R_1$ is C(O)—$C_1$-$C_6$ alkyl or C(O)—$C_3$-$C_5$ cycloalkyl;
$R_3$, $R_4$, $R_5$ and $R_6$ are, independently, selected from among H, halogen, $C_1$-$C_6$ alkyl, and O—$C_1$-$C_6$ alkyl; and
$R_7$ is H or $C_1$-$C_6$ alkyl.

In a further embodiment, the compound has the structure of formula I, wherein:
$R_1$ is C(O)$C_1$-$C_4$ alkyl or C(O)$C_3$-$C_6$ cycloalkyl;
$R_3$, $R_4$, $R_5$ and $R_6$ are H; and $R_7$ is $C_1$ alkyl.

In still a further embodiment, the compound has the structure of formula I, wherein $R_1$ or $R_2$ is CN.

In another embodiment, the compound is N-[4-(5-cyano-1-methyl-1H-pyrrol-2-yl)phenyl]-2-furamide; N-[4-(5-cyano-1-methyl-1H-pyrrol-2-yl)phenyl]-3-methylbutanamide; N-[4-(5-cyano-1-methyl-1H-pyrrol-2-yl)phenyl]-2-methylpropanamide; N-[4-(5-cyano-1-methyl-1H-pyrrol-2-yl)phenyl]propanamide; N-[4-(5-cyano-1-methyl-1H-pyrrol-2-yl)phenyl]butanamide; N-[4-(5-cyano-1-methyl-1H-pyrrol-2-yl)phenyl]acetamide; N-[4-(5-cyano-1-methyl-1H-pyrrol-2-yl)phenyl]benzamide; N-[4-(5-cyano-1-methyl-1H-pyrrol-2-yl)phenyl]cyclobutanecarboxamide; N-[4-(5-cyano-1-methyl-1H-pyrrol-2-yl)phenyl]cyclohexanecarboxamide; N-[4-(5-cyano-1-methyl-1H-pyrrol-2-yl)phenyl]-2-methylacrylamide; Ethyl[4-(5-cyano-1-methyl-1H-pyrrol-2-yl)phenyl]carbamate; Isobutyl[4-(5-cyano-1-methyl-1H-pyrrol-2-yl)phenyl]carbamate; N,N'-bis[4-(5-cyano-1-methyl-1H-pyrrol-2-yl)phenyl]urea; [4-(5-cyano-1-methyl-1H-pyrrol-2-yl)-2-methylphenyl]cyanamide; [4-(5-cyano-1-methyl-1H-pyrrol-2-yl)-2-ethylphenyl]cyanamide; [4-(5-cyano-1-methyl-1H-pyrrol-2-yl)-2-propylphenyl]cyanamide; [4-(5-cyano-1-methyl-1H-pyrrol-2-yl)-2-isopropylphenyl]cyanamide; [2-chloro-4-(5-cyano-1-methyl-1H-pyrrol-2-yl)phenyl]cyanamide; [2-fluoro-4-(5-cyano-1-methyl-1H-pyrrol-2-yl)phenyl]cyanamide; [4-(5-cyano-1-methyl-1H-pyrrol-2-yl)-2-methoxyphenyl]cyanamide; [4-(5-cyano-1-methyl-1H-pyrrol-2-yl)-3-methoxyphenyl]cyanamide; [4-(5-cyano-1-methyl-1H-pyrrol-2-yl)-3-methylphenyl]cyanamide; and [4-(5-cyano-1-methyl-1H-pyrrol-2-yl)phenyl]methylcyanamide.

The compounds can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups. In one embodiment, an alkyl group has 1 to about 8 carbon atoms (i.e., $C_1$, $C_2$, $C_3$, $C_4$, $C_5$ $C_6$, $C_7$, or $C_8$). In another embodiment, an alkyl group has 1 to about 6 carbon atoms (i.e., $C_1$, $C_2$, $C_3$, $C_4$, $C_5$ or $C_6$). In a further embodiment, an alkyl group has 1 to about 4 carbon atoms (i.e., $C_1$, $C_2$, $C_3$, or $C_4$).

The term "cycloalkyl" is used herein to refer to cyclic, saturated aliphatic hydrocarbon groups. In one embodiment, a cycloalkyl group has 3 to about 8 carbon atoms (i.e., $C_3$, $C_4$, $C_5$, $C_6$, $C_7$, or $C_8$). In another embodiment, a cycloalkyl group has 3 to about 6 carbon atoms (i.e., $C_3$, $C_4$, $C_5$ or $C_6$).

The term "alkenyl" is used herein to refer to both straight- and branched-chain alkyl groups having one or more carbon-carbon double bonds. In one embodiment, an alkenyl group contains 3 to about 8 carbon atoms (i.e., $C_3$, $C_4$, $C_5$, $C_6$, $C_7$, or $C_8$). In another embodiment, an alkenyl groups has 1 or 2 carbon-carbon double bonds and 3 to about 6 carbon atoms (i.e., $C_3$, $C_4$, $C_5$ or $C_6$).

The term "alkynyl" group is used herein to refer to both straight- and branched-chain alkyl groups having one or more carbon-carbon triple bonds. In one embodiment, an alkynyl group has 3 to about 8 carbon atoms (i.e., $C_3$, $C_4$, $C_5$, $C_6$, $C_7$, or $C_8$). In another embodiment, an alkynyl group contains 1 or 2 carbon-carbon triple bonds and 3 to about 6 carbon atoms (i.e., $C_3$, $C_4$, $C_5$, or $C_6$).

The terms "substituted alkyl", "substituted alkenyl", "substituted alkynyl", and "substituted cycloalkyl" refer to alkyl, alkenyl, alkynyl, and cycloalkyl groups, respectively, having one or more substituents including, without limitation, halogen, CN, OH, $NO_2$, amino, aryl, heterocyclic groups, aryl, alkoxy, aryloxy, alkyloxy, alkylcarbonyl, alkylcarboxy, amino, and arylthio.

The term "aryl" as used herein refers to an aromatic, carbocyclic system, e.g., of about 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be substituted. Desirably, a substituted aryl group is substituted with 1 to about 4 substituents.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio. A substituted heterocycle or heteroaryl group may have 1, 2, 3, or 4 substituents.

The term "arylthio" as used herein refers to the S(aryl) group, where the point of attachment is through the sulfur-atom and the aryl group can be substituted as noted above. The term "alkoxy" as used herein refers to the O(alkyl) group, where the point of attachment is through the oxygen-atom and the alkyl group can be substituted as noted above. The term "aryloxy" as used herein refers to the O(aryl) group, where the point of attachment is through the oxygen-atom and the aryl group can be substituted as noted above.

The term "alkylcarbonyl" as used herein refers to the C(O)(alkyl) group, where the point of attachment is through the carbon-atom of the carbonyl moiety and the alkyl group can be substituted as noted above.

The term "alkylcarboxy" as used herein refers to the C(O)O(alkyl) group, where the point of attachment is through the carbon-atom of the carboxy moiety and the alkyl group can be substituted as noted above.

The term "alkylamino" as used herein refers to both secondary and tertiary amines where the point of attachment is through the nitrogen-atom and the alkyl groups can be substituted as noted above. The alkyl groups can be the same or different.

The term "halogen" as used herein refers to Cl, Br, F, or I groups.

The compounds encompass tautomeric forms of the structures provided herein characterized by the bioactivity of the drawn structures. Further, the compounds can be used in the form of salts derived from pharmaceutically or physiologically acceptable acids, bases, alkali metals and alkaline earth metals.

Pharmaceutically acceptable salts may be formed from inorganic bases, desirably alkali metal salts, for example, sodium, lithium, or potassium, and organic bases, such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butyl-monoethanolammonium, tris(hydroxymethyl)methylammonium, phenylmono-ethanolammonium, and the like. Physiologically acceptable alkali salts and alkaline earth metal salts can include, without limitation, sodium, potassium, calcium and magnesium salts in the form of esters, and carbamates.

Other conventional "pro-drug" forms can also be utilized which, when delivered in such form, convert to the active moiety in vivo. Such other compounds can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Med. Research Rev., 16(3):233-241, ed., John Wiley & Sons (1996).

As described herein, the compounds of formula I and/or salts, prodrugs or tautomers thereof, are delivered in regimens for contraception, therapeutic or prophylactic purposes, as described herein.

The compounds discussed herein also encompass "metabolites" which are unique products formed by processing the compounds described herein by the cell or patient. Desirably, metabolites are formed in vivo.

The compounds are readily prepared by one of skill in the art according to the following schemes from commercially available starting materials or starting materials which can be prepared using literature procedures. These schemes show the preparation of representative compounds. Variations on these methods or other methods known in the art can be readily utilized by one of skill in the art given the information provided herein.

Scheme 1

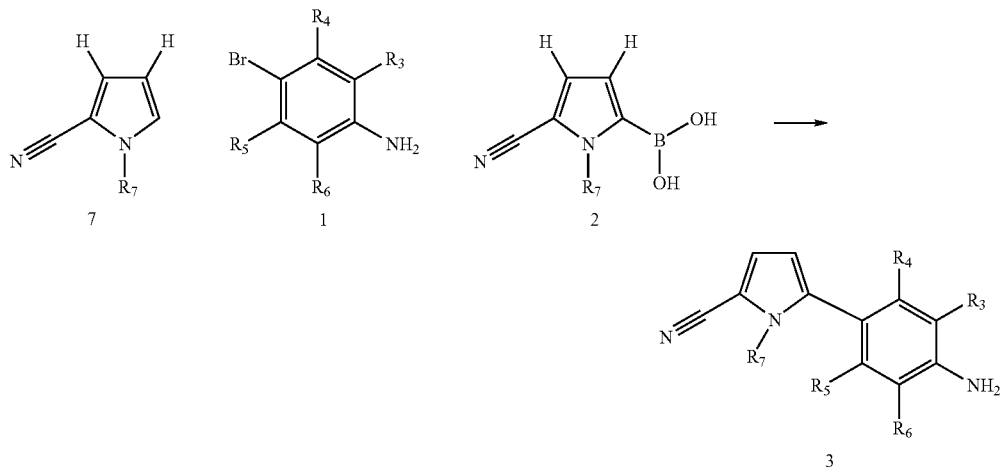

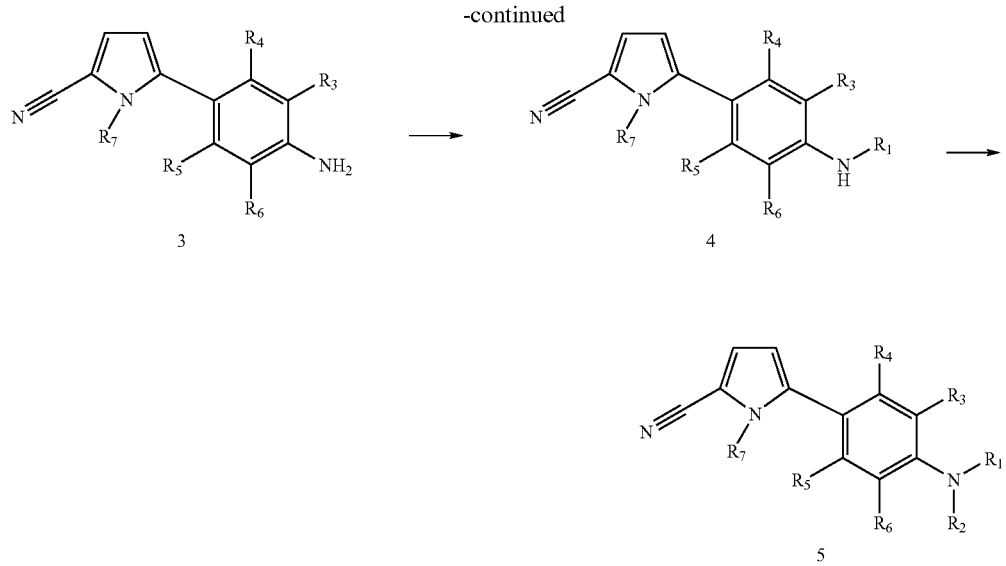

According to scheme 1, an appropriately substituted bromoaniline (1) is converted into compound 3 under the action of a palladium catalyst and a suitable coupling partner such as a boronic acid or tin derivative. The aniline may also be a chloro, iodo, or sulfonate derivative. The coupling partner may be formed in situ from the pyrrole (7) and lithium diisopropylamide and a trialkyl borate or may be the preformed boronic acid (2) as described in co-owned US Patent Application Publication No. US-2005-0272702-A1, which is hereby incorporated by reference. The source of palladium is normally tetrakis(triphenylphosphine) palladium (0) or another suitable source such as palladium dibenzylidene acetone in the presence of tributylphosphine (Fu, G. C. et al. Journal of the American Chemical Society, 2000, 122, 4020). Alternate catalyst systems are described in Hartwig et al., Journal of Organic Chemistry, 2002, 67, 5553. A base is also required in the reaction; the normal choices are sodium or potassium carbonate, cesium fluoride, potassium fluoride, or potassium phosphate. The choice of solvents includes THF, dimethoxy ethane, dioxane, ethanol, water, and toluene. Depending on the reactivity of the coupling partners and reagents, the reaction may be conducted up to the boiling point of the solvents, or may indeed be accelerated under microwave irradiation, if necessary.

Compounds 4, where $R_1$ includes an amide, are readily accessible from 3 by reaction with a wide variety of electrophilic reagents including acid chlorides and carboxylic acids combined with an activating reagent such as dicyclohexyl-carbodiimide (DCC), N-(3-dimethylaminopropyl)-N'-ethylcarbodiimide hydrochloride (EDC), benzotriazol-1-yl-oxytripyrrolidinophosphonium hexafluorophosphate (the PyBOP® reagent); or for further examples see, e.g., R. C. Larock, "Comprehensive Organic Transformations", Second Edition, John Wiley & Sons (1999). Compounds 4, where $R_1$ includes a carbamate, are readily accessible from compounds 3 by reaction with a wide variety of electrophilic reagents including chloroformates or activated carbonates. Compounds 4, where $R_1$ includes a cyanamide, are readily accessible from compounds 3 by reaction with electrophilic reagents such as cyanogen bromide. Compounds 4, where $R_1$ includes a urea, are readily accessible from compounds 3 by reaction with a wide variety of electrophilic reagents including phosgene, carbamoyl chlorides, and isocyanates. These reactions are conducted in a suitable solvent including methylene chloride, THF, dimethylformamide (DMF), or pyridine in the presence of an amine base such as pyridine, triethylamine, or diisopropylethyl amine. Metal salts including sodium carbonate, cesium carbonate, potassium carbonate, are also suitable bases for the reaction. The aniline 3 may also be pretreated with a strong base, including alkyl lithium bases, potassium tertiary butoxide, sodium hexamethyldisilazide and similar bases in an aprotic solvent such as ether or THF and then reacted with the electrophilic reagent. Alternatively, the aniline 3 may be directly dissolved in an acid chloride or chloroformate in the absence of solvent or base to generate compounds 4.

Compounds 5 are readily accessible from compounds 4 by reaction with a wide variety of electrophilic reagents such as acid chlorides, chloroformates, cyanogen bromide, isocyanates, and alkylating agents. Alkylating agents are commonly comprised of an alkane possessing a suitable leaving group such as a bromide, iodide, chloride, or sulfonate. Common examples of alkylating agents are methyl iodide, benzyl bromide, propyl bromide, allyl chloride, and propargyl bromide. The corresponding carboxylic acid derivative and a suitable activating reagent can also be reacted with compounds 4 to give compounds 5. These reactions are conducted in a suitable solvent including methylene chloride, THF, DMF, or pyridine in the presence of an amine base such as pyridine, triethylamine, or diisopropylethyl amine. Metal salts including sodium carbonate, cesium carbonate, or potassium carbonate are also suitable bases for the reaction. The aniline derivative 4 may also be pretreated with a strong base, including alkyl lithium bases, potassium tertiary butoxide, sodium hexamethyldisilazide and similar bases in an aprotic solvent such as ether or THF and then reacted with the electrophilic reagent. Alternatively the aniline derivative 4 may be directly dissolved in an acid chloride, chloroformate in the absence of solvent or base to generate compounds 5.

Scheme 2

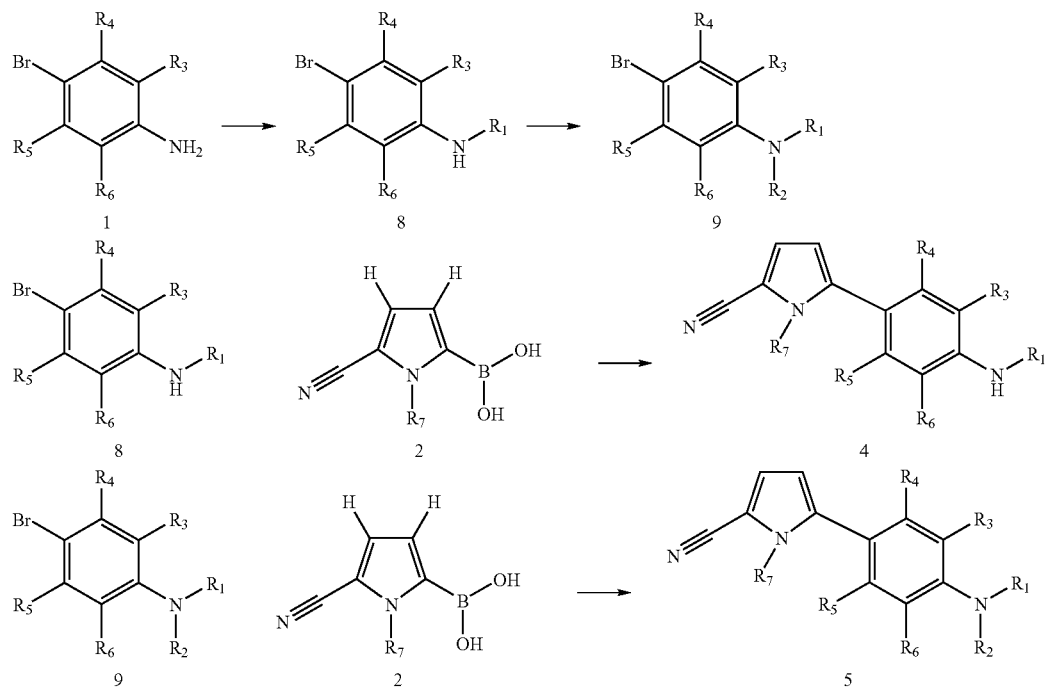

An alternative method for the production of compounds 4 and 5 is shown in Scheme 2. Compounds 8, where $R_1$ includes an amide, are readily accessible from aniline 1 by reaction with a wide variety of electrophilic reagents including acid chlorides and carboxylic acids combined with an activating reagent. Compounds 8, where $R_1$ includes a carbamate, are readily accessible from aniline 1 by reaction with a wide variety of electrophilic reagents including chloroformates or activated carbonates. Compounds 8, where $R_1$ includes a cyanamide, are readily accessible from aniline 1 by reaction electrophilic reagents such as cyanogen bromide. Compounds 8, where $R_1$ includes a urea, are readily accessible from aniline 1 by reaction with a wide variety of electrophilic reagents including phosgene, carbamoyl chlorides, and isocyanates. These reactions are conducted in a suitable solvent including methylene chloride, THF, DMF, or pyridine in the presence of an amine base such as pyridine, triethylamine, or diisopropylethyl amine. Metal salts including sodium carbonate, cesium carbonate, or potassium carbonate are also suitable bases for the reaction. The aniline 1 may also be pretreated with a strong base, including alkyl lithium bases, potassium tertiary butoxide, sodium hexamethyldisilazide and similar bases in an aprotic solvent such as ether or THF and then reacted with the electrophilic reagent. Alternatively the aniline 1 may be directly dissolved in an acid chloride or chloroformate in the absence of solvent or base to generate compounds 8.

Bromoaniline compounds 9 are readily accessible from substituted bromoaniline compounds 8 by reaction with a wide variety of electrophilic reagents such as acid chlorides, chloroformates, cyanogen bromide, isocyanates, and alkylating agents. Alkylating agents are commonly comprised of an alkane possessing a suitable leaving group such as a bromide, iodide, chloride, or sulfonate. Common examples of alkylating agents are methyl iodide, benzyl bromide, propyl bromide, allyl chloride, and propargyl bromide. The corresponding carboxylic acid derivative and a suitable activating reagent can also be reacted with compounds 8 to give compounds 9. These reactions are conducted in a suitable solvent including methylene chloride, THF, DMF, or pyridine in the presence of an amine base such as pyridine, triethylamine, or diisopropylethyl amine. Metal salts including sodium carbonate, cesium carbonate, potassium carbonate, are also suitable bases for the reaction. The aniline derivative 8 may also be pretreated with a strong base, including alkyl lithium bases, potassium tertiary butoxide, sodium hexamethyldisilazide and similar bases in an aprotic solvent such as ether or THF and then reacted with the electrophilic reagent. Alternatively the aniline derivative 8 may be directly dissolved in an acid chloride or chloroformate in the absence of solvent or base to generate compounds 9.

The substituted bromoaniline 8 or bromoaniline 9 is converted into compound 4 or compound 5 respectively, under the action of a palladium catalyst and a suitable coupling partner such as a boronic acid or tin derivative. The aniline may also be a chloro, iodo, or sulfonate derivative. The coupling partner may be formed in situ from the pyrrole (7) (see, scheme 1) and lithium diisopropylamide and a trialkyl borate or may be the pre-formed boronic acid 2. The source of palladium is normally tetrakis(triphenylphosphine) palladium (0) or another suitable source such as palladium dibenzylidene acetone in the presence of tributylphosphine (Fu, G. C. et al. Journal of the American Chemical Society, 2000, 122, 4020, for alternate catalyst systems see also Hartwig, J. F. et al. *Journal of Organic Chemistry*, 2002, 67, 5553). A base is also required in the reaction and the normal choices are sodium or potassium carbonate, cesium fluoride, potassium fluoride, or potassium phosphate. The choice of solvents includes THF, dimethoxy ethane, dioxane, ethanol, water, and toluene. Depending on the reactivity of the coupling partners and reagents, the reaction may be conducted up to the boiling point of the solvents, or may indeed be accelerated under microwave irradiation, if necessary.

Also provided are pharmaceutical compositions containing one or more compounds described herein and a pharmaceutically acceptable carrier or excipient. These compounds and compositions can be used in methods of treatment which include administering to a mammal a pharmaceutically effective amount of one or more compounds as described above as modulators of the progesterone receptor.

The compounds can be utilized in methods of contraception, hormone replacement therapy and the treatment and/or prevention of benign and malignant neoplastic disease, uterine myometrial fibroids, endometriosis, benign prostatic hypertrophy, carcinomas and adenocarcinomas of the endometrium, ovary, breast, colon, prostate, pituitary, meningioma and other hormone-dependent tumors, dysmenorrhea, dysfunctional uterine bleeding, cycle-related symptoms, and symptoms of premenstrual syndrome and premenstrual dysphoric disorder; and for inducing amenorrhea. Additional uses of the present progesterone receptor modulators include the synchronization of the estrus in livestock.

The term "cycle-related symptoms" refers to psychological and physical symptoms associated with a woman's menstrual cycle arising in the luteal phase of the menstrual cycle. It has been reported that most women report experiencing cycle-related symptoms. The symptoms generally disappear after the onset of menstruation, and the patient is free from symptoms during the rest of the follicular phase. The cyclical nature of the symptom variations is characteristic of cycle-related symptoms.

Cycle-related symptoms occur in about 95% of women who experience some physical or mood changes with their menstrual cycles. Only about one-third of those women experiences moderate to severe cycle-related symptoms. Women vary in the number, type, severity, and pattern of symptoms before menstruation. One thing common to all the types of cyclic-related symptoms is the decrease or elimination of the symptoms in the two weeks after menstruation up to ovulation.

The term "cycle-related symptoms" refers to psychological symptoms (for example, mood change, irritability, anxiety, lack of concentration, or decrease in sexual desire) and physical symptoms (for example, dysmenorrhea, breast tenderness, bloating, fatigue, or food cravings) associated with a woman's menstrual cycle. Cycle-related symptoms occur after ovulation but before menses and usually terminate at the start of the menstrual period or shortly thereafter. Cycle-related symptoms include, but are not limited to, dysmenorrhea and moderate to severe cycle-related symptoms.

Suitably, the PR modulators are formulated for delivery by any suitable route including, e.g., transdermal, mucosal (intranasal, buccal, vaginal), oral, parenteral, etc, by any suitable delivery device including, e.g., transdermal patches, topical creams or gels, a vaginal ring, among others.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. In one embodiment, satisfactory results are obtained when the compounds are administered at a daily dosage of from about 0.5 to about 500 mg/kg of animal body weight, desirably given in divided doses one to four times a day, or in a sustained release form. For most large mammals, the total daily dosage is from about 1 to 100 mg, desirably from about 2 to 80 mg. Dosage forms suitable for internal use contain from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, butylated hydroxytoluene (BHT) and butylated hydroxyanisole (BHA).

The pharmaceutical compositions from the standpoint of ease of preparation and administration are solid compositions, particularly tablets and hard-filled or liquid-filled capsules. Oral administration of the compounds is desirable.

The compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The compounds may also be administered via a vaginal ring. Suitably, use of the vaginal ring is timed to the 28 day cycle. In one embodiment, the ring is inserted into the vagina, and it remains in place for 3 weeks. During the fourth week, the vaginal ring is removed and menses occurs. The following week a new ring is inserted to be worn another 3 weeks until it is time for the next period. In another embodiment, the vaginal ring is inserted weekly, and is replaced for three consecutive weeks. Then, following one week without the ring, a new ring is inserted to begin a new regimen. In yet another embodiment, the vaginal ring is inserted for longer or shorter periods of time.

For use in the vaginal ring, a PR modulator compound is formulated in a manner similar to that described for contraceptive compounds previously described for delivery via a vaginal ring. See, e.g., U.S. Pat. Nos. 5,972,372; 6,126,958 and 6,125,850.

The PR modulator compound(s) may also be delivered via a transdermal patch. Suitably, use of the patch is timed to the 28 day cycle. In one embodiment, the patch is applied via a suitable adhesive on the skin, where it remains in place for 1 week and is replaced weekly for a total period of three weeks. During the fourth week, no patch is applied and menses occurs. The following week a new patch is applied to be worn to begin a new regimen. In yet another embodiment, the patch remains in place for longer, or shorter periods of time.

In one embodiment, the PR modulator(s) are used in cyclic regimens involving administration of the PR modulator alone. In another embodiment, the cyclic regimen involves administration of a PR modulator in combination with an estrogen or progestin, or both. Particularly desirable progestins can be selected from among those described in U.S. Pat. Nos. 6,355,648; 6,521,657; 6,436,929; 6,540,710; and 6,562,857 and US Patent Application Publication No. 2004-0006060-A1. Still other progestins are known in the art and can be readily selected. In one embodiment, combination regimens with the PR agonist (i.e., progestin) tanaproget 5-(4,4-dimethyl-2-thioxo-1,4-dihydro-2H-3,1-benzoxazin-6-yl)-1-methyl-1H-pyrrole-2-carbonitrile are provided.

Further provided are administration regimens carried out over 28 consecutive days. These regimens may be continuous or may involve a terminal portion of the cycle, e.g., 0 to 7 days, containing administration of no progestins, estrogens or anti-progestins. See, e.g., the regimens described in US Patent Application Publication No. US-2006-0009509-A1, which is hereby incorporated by reference.

The regimens described herein may be utilized for contraception, or for any of the other indications described herein. Where administration is for contraception, the compositions may be formulated in oral dosage units.

When utilized for contraception, the PR modulators may be administered to a female of child bearing age, alone or in combination with an estrogen. For the first 14 to 24 days of the cycle, a progestational agent is administered, desirably at a dosage range equal in progestational activity to about 35 µg to about 150 µg levonorgestrel per day, and more desirably equal in activity to about 35 µg to about 100 µg levonorgestrel per day. A PR modulator may then be administered alone or in combination with an estrogen for a period of 1 to 11 days to begin on any cycle day between day 14 and 24. The PR modulator in these combinations may be administered at a dose of from about 2 µg to about 50 µg per day and the estrogen may be administered at a dose of from about 10 µg to about 35 µg per day. In an oral administration, a package or kit containing 28 tablets will include a placebo tablet on those days when the PR modulator, progestin, or estrogen is not administered.

Progestational agents include, but are not limited to, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Among the desirable progestins for use in the combinations are levonorgestrel, gestodene and trimegestone.

Examples of orally administered regimens over a 28 day cycle include administration of a progestational agent solely for the first 21 days at a daily dose equal in progestational activity to from about 35 to about 100 µg of levonorgestrel. A PR modulator compound can then be administered at a daily dose of from about 1 to 200 mg from day 22 to day 24, followed by no administration or administration of a placebo for days 25 to 28. It is most desirable that the daily dosages of each relevant active ingredient be incorporated into a combined, single daily dosage unit, totaling 28 daily units per 28-day cycle.

In another regimen, a progestational agent may be coadministered for the first 21 days at a daily dose equal in progestational activity to from about 35 to about 150 µg levonorgestrel, desirably equal in activity to from about 35 to about 100 µg levonorgestrel, with an estrogen, such as ethinyl estradiol, at a daily dose range of from about 10 to about 35 µg. This may be followed as described above with a PR modulator administered at a daily dose of from about 1 to 250 mg from day 22 to day 24, followed by no administration or administration of a placebo for days 25 to 28.

Still another regimen can include co-administration from days 1 to 21 of a progestational agent, e.g., levonorgestrel, being administered at a daily dose equal in progestational activity to from about 35 to about 100 µg levonorgestrel, and an estrogen, such as ethinyl estradiol, at a daily dose range of from about 10 to about 35 µg. This will be followed on days 22 to 24 by coadministration of a PR modulator (1 to 250 mg/day) and an estrogen, such as ethinyl estradiol, at a daily dose of from about 10 to about 35 µg. From day 25 to day 28, this regimen may be followed by no administration or administration of a placebo.

The compounds and compositions can be included in kits or packages of pharmaceutical formulations designed for use in the regimens described herein. These kits are desirably designed for daily oral administration over a 28-day cycle, desirably for one oral administration per day, and organized so as to indicate a single oral formulation or combination of oral formulations to be taken on each day of the 28-day cycle. Desirably, each kit will include oral tablets to be taken on each the days specified. Desirably, one oral tablet will contain each of the combined daily dosages indicated.

According to the regimens described above, one 28-day kit may include (a) an initial phase of from 14 to 21 daily dosage units of a progestational agent equal in progestational activity to about 35 to about 150 µg levonorgestrel, desirably equal in progestational activity to about 35 to about 100 µg levonorgestrel; (b) a second phase of from 1 to 11 daily dosage units of a PR modulator compound, each daily dosage unit containing the PR modulator compound at a daily dosage of from about 1 to 250 mg; and (c) optionally, a third phase of an orally and pharmaceutically acceptable placebo for the remaining days of the cycle in which no PR modulator (i.e., antiprogestin or progestin) or estrogen is administered.

In one embodiment of this kit, the initial phase involves 21 daily dosage units as described in the preceding passage, a second phase of 3 daily dosage units for days 22 to 24 of a PR modulator compound and an optional third phase of 4 daily units of an orally and pharmaceutically acceptable placebo for each of days 25 to 28.

In another embodiment, a 28-day cycle packaged regimen or kit contains a first phase of from 18 to 21 daily dosage units, and more desirably, 21 days, as described in the preceding passages, and, further including, as an estrogen, ethinyl estradiol at a daily dose range of from about 10 to about 35 μg; a second phase of from 1 to 7 daily dosage units, and desirably, 4 daily dosage units, as described above, and an optional placebo for each of the remaining 0-9 days, or about 4 days, in the 28-day cycle in which no progestational agent, estrogen or antiprogestin is administered.

A further 28-day packaged regimen or kit includes (a) a first phase of from 18 to 21 daily dosage units, each containing a progestational agent at a daily dose equal in progestational activity to about 35 to about 150 μg levonorgestrel, desirably equal in activity to from about 35 to about 100 μg levonorgestrel, and ethinyl estradiol at a daily dose range of from about 10 to about 35 μg; (b) a second phase of from 1 to 7 daily dose units, each daily dose unit containing a PR modulator at a concentration of from 1 to 250 mg and ethinyl estradiol at a concentration of from about 10 to about 35 μg; and (c) optionally, an orally and pharmaceutically acceptable placebo for each of the remaining 0-9 days in the 28-day cycle in which no progestational agent, estrogen or antiprogestin is administered.

In one embodiment, the package or kit just described includes a first phase of 21 daily dosage units; a second phase of 3 daily dosage units for days 22 to 24, each daily dose unit containing an PR modulator at a concentration of from 2 to 200 mg and ethinyl estradiol at a concentration of from about 10 to about 35 μg; and optionally, a third phase of 4 daily units of an orally and pharmaceutically acceptable placebo for each of days 25 to 28.

In each of the regimens and kits just described, it is desirable that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also desirable that the kits contain the placebo described for the final days of the cycle. It is further desirable that each package or kit include a pharmaceutically acceptable package having indicators for each day of the 28-day cycle, such as a labeled blister package or dial dispenser packages known in the art.

As used herein, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

The desirable pharmaceutical compositions from the standpoint of ease of preparation and administration are solid compositions, particularly tablets and hard-filled or liquid-filled capsules. Oral administration of the compounds is desirable.

The compounds and compositions can further be provided in kits and delivery devices for a variety of other therapeutic uses as described herein including, e.g., hormone replacement therapy, the treatment and/or prevention of benign and malignant neoplastic disease. Such kits contain components in addition to the compounds, including, e.g., instructions for delivery of the compounds, diluents, vials, syringes, packaging, among other items.

Such kits may optionally be adapted for the selected application, e.g., hormone replacement therapy, treatment and/or prevention of uterine myometrial fibroids, endometriosis, benign prostatic hypertrophy, carcinomas and adenocarcinomas of the endometrium, ovary, breast, colon, prostate, pituitary, meningioma and other hormone-dependent tumors, dysmenorrheal, dysfunctional uterine bleeding, cycle-related symptoms, and symptoms of premenstrual syndrome and premenstrual dysphoric disorder, or the synchronization of the estrus in livestock.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

5-(4-aminophenyl)-1-methyl-1H-pyrrole-2-carbonitrile

4-Bromoaniline (5.00 g, 29.0 mmol), 1-methyl-5-cyano-2-pyrroleboronic acid (5.2 g, 34.8 mmol), KF (5.55 g, 95.7 mmol), and $Pd_2(dba)_3$ (332 mg, 0.36 mmol) were added to a 200 mL round bottom flask under nitrogen. The flask was sealed and purged with nitrogen for 5 min. THF (72 mL) was added and the mixture was purged with nitrogen for an additional 5 min. A solution of tri-t-butylphosphine (10 wt % in hexanes) (2.15 mL, 0.73 mmol) was added via syringe and the mixture was stirred vigorously at 25° C. for 5 h. The mixture was diluted with 250 mL of EtOAc, filtered through a plug of silica gel, washed through with 200 mL of EtOAc and concentrated to give a crude brown/black semi-solid. Purification by silica gel flash chromatography (20% acetone/hexane) afforded 5-(4-aminophenyl)-1-methyl-1H-pyrrole-2-carbonitrile (3.3 g) as an off-white solid.

HPLC purity 100% at 210-370 nm, 7.6 min.; 100% at 290 nm, 7.6 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{12}H_{11}N_3+H^+$, 198.10257. found (ESI, [M+H]$^+$), 198.1027.

Example 2

5-(4-amino-3-fluorophenyl)-1-methyl-1H-pyrrole-2-carbonitrile

4-Bromo-2-fluoroaniline (2.42 g, 12.8 mmol), 1-methyl-5-cyano-2-pyrroleboronic acid (2.3 g, 15.3 mmol), KF (2.45 g, 42.2 mmol), and $Pd_2(dba)_3$ (147 mg, 0.16 mmol) were added to a 100 mL round bottom flask under nitrogen. The flask was sealed and purged with nitrogen for 5 min. THF (32 mL) was added and the mixture was purged with nitrogen for an additional 5 min. A solution of tri-t-butylphosphine (10 wt % in hexanes) (0.95 mL, 0.32 mmol)

was added via syringe and the mixture was stirred vigorously at 25° C. for 5 h. The mixture was diluted with 250 mL of EtOAc, filtered through a plug of silica gel, washed through with 200 mL of EtOAc and concentrated to give a crude brown/black semi-solid. Purification by flash chromatography (20% acetone/hexane) afforded 5-(4-amino-3-fluorophenyl)-1-methyl-1H-pyrrole-2-carbonitrile (0.76 g) as an off-white solid.

HPLC purity 100% at 210-370 nm, 8.4 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{12}H_{10}FN_3+H^+$, 216.09315. found (ESI, [M+H]$^+$), 216.0947

Example 3

N-[4-(5-cyano-1-methyl-1H-pyrrol-2-yl)phenyl]-2-furamide

The general procedure for acylation of 5-(4-aminophenyl)-1-methyl-1H-pyrrole-2-carbonitrile is as follows.

5-(4-Aminophenyl)-1-methyl-1H-pyrrole-2-carbonitrile (98 mg, 0.5 mmol) was dissolved in dichloromethane (2 mL) and triethylamine (87 μL, 0.6 mmol) was added. Furan-2-carbonyl chloride (54 μL, 0.55 mmol) was added and the mixture was stirred 16 hours. The mixture was diluted with 50% ether in ethyl acetate and washed with water, saturated NaHCO$_3$, 2N HCl, brine, dried over MgSO$_4$, and passed through a plug of silica gel. The solution was concentrated to give N-[4-(5-cyano-1-methyl-1H-pyrrol-2-yl)phenyl]-2-furamide (0.041 g).

HPLC purity 100% at 210-370 nm, 8.9 min.; 100% at 302 nm, 8.9 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{17}H_{13}N_3O_2+H^+$, 292.10805. found (ESI, [M+H]$^+$), 292.1072.

Example 4:

N-[4-(5-cyano-1-methyl-1H-pyrrol-2-yl)phenyl]-3-methylbutanamide

The title compound was prepared according to the general procedure for acylation of 5-(4-aminophenyl)-1-methyl-1H-pyrrole-2-carbonitrile using 3-methyl-butyryl chloride (67 μL, 0.55 mmol) to provide N-[4-(5-cyano-1-methyl-1H-pyrrol-2-yl)phenyl]-3-methyl butanamide (0.042 g).

HPLC purity 100% at 210-370 nm, 9.4 min.; 99.6% at 290 nm, 9.4 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{17}H_{19}N_3O+H^+$, 282.16009; found (ESI, [M+H]$^+$), 282.1608.

Example 5

N-[4-(5-cyano-1-methyl-1H-pyrrol-2-yl)phenyl]-2-methylpropanamide

The title compound was prepared according to the general procedure for acylation of 5-(4-aminophenyl)-1-methyl-1H-pyrrole-2-carbonitrile using isobutyryl chloride (58 μL, 0.55 mmol) to provide N-[4-(5-cyano-1-methyl-1H-pyrrol-2-yl)phenyl]-2-methylpropanamide (0.026 g).

HPLC purity 100% at 210-370 nm, 8.9 min.; 100% at 290 nm, 8.9 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{16}H_{17}N_3O+H^+$, 268.14444; found (ESI, [M+H]$^+$), 268.1433.

Example 6

N-[4-(5-cyano-1-methyl-1H-pyrrol-2-yl)phenyl]propanamide

The title compound was prepared according to the general procedure for acylation of 5-(4-aminophenyl)-1-methyl-1H-pyrrole-2-carbonitrile using propionyl chloride (48 μL, 0.55 mmol) to provide N-[4-(5-cyano-1-methyl-1H-pyrrol-2-yl)phenyl]propanamide (0.012 g).

HPLC purity 100% at 210-370 nm, 8.4 min.; 99.7% at 290 nm, 8.4 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{15}H_{15}N_3O+H^+$, 254.12879; found (ESI, [M+H]$^+$), 254.1293.

Example 7

N-[4-(5-cyano-1-methyl-1H-pyrrol-2-yl)phenyl]butanamide

The title compound was prepared according to the general procedure for acylation of 5-(4-aminophenyl)-1-methyl-1H-pyrrole-2-carbonitrile using butyryl chloride (59 μL, 0.55 mmol) to provide N-[4-(5-cyano-1-methyl-1H-pyrrol-2-yl)phenyl]butanamide (0.045 g).

HPLC purity 100% at 210-370 nm, 9.0 min.; 99.9% at 272 nm, 9.0 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{16}H_{17}N_3O+H^+$, 268.14444; found (ESI, [M+H]$^+$), 268.1432.

Example 8

N-[4-(5-cyano-1-methyl-1H-pyrrol-2-yl)phenyl]acetamide

The title compound was prepared according to the general procedure for acylation of 5-(4-aminophenyl)-1-methyl-1H-pyrrole-2-carbonitrile using acetyl chloride (39 μL, 0.55 mmol) to provide N-[4-(5-cyano-1-methyl-1H-pyrrol-2-yl)phenyl]acetamide (0.018 g).

HPLC purity 100% at 210-370 nm, 7.8 min.; 100% at 290 nm, 7.8 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{14}H_{13}N_3O+H^+$, 240.11314; found (ESI, [M+H]$^+$), 240.1135.

Example 9

N-[4-(5-cyano-1-methyl-1H-pyrrol-2-yl)phenyl]benzamide

The title compound was prepared according to the general procedure for acylation of 5-(4-aminophenyl)-1-methyl-1H-pyrrole-2-carbonitrile using benzoyl chloride (64 μL, 0.55 mmol) to provide N-[4-(5-cyano-1-methyl-1H-pyrrol-2-yl)phenyl]benzamide (0.035 g).

HPLC purity 97.4% at 210-370 nm, 9.6 min.; 97.2% at 298 nm, 9.6 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{19}H_{15}N_3O+H^+$, 302.12879; found (ESI, [M+H]$^+$), 302.1273.

Example 10

N-[4-(5-cyano-1-methyl-1H-pyrrol-2-yl)phenyl]cyclobutane-carboxamide

The title compound was prepared according to the general procedure for acylation of 5-(4-aminophenyl)-1-methyl-1H-pyrrole-2-carbonitrile using cyclobutane carbonyl chloride (60 μL, 0.55 mmol) to provide N-[4-(5-cyano-1-methyl-1H-pyrrol-2-yl)phenyl]cyclobutane carboxamide (0.048 g).

HPLC purity 99.5% at 210-370 nm, 9.3 min.; 99.5% at 290 nm, 9.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{17}H_{17}N_3O+H^+$, 280.14444; found (ESI, [M+H]$^+$), 280.145.

Example 11

N-[4-(5-cyano-1-methyl-1H-pyrrol-2-yl)phenyl]cyclohexane-carboxamide

The title compound was prepared according to the general procedure for acylation of 5-(4-aminophenyl)-1-methyl-1H-pyrrole-2-carbonitrile using cyclohexanecarbonyl chloride (67 μL, 0.55 mmol) to provide N-[4-(5-cyano-1-methyl-1H-pyrrol-2-yl)phenyl]cyclohexanecarboxamide (0.039 g).

HPLC purity 99.5% at 210-370 nm 10.1 min.; 99.6% at 290 nm, 10.1 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{19}H_{21}N_3O+H^+$, 308.17574; found (ESI, [M+H]$^+$), 308.1764.

Example 12

N-[4-(5-cyano-1-methyl-1H-pyrrol-2-yl)phenyl]-2-methylacrylamide

The title compound was prepared according to the general procedure for acylation of 5-(4-aminophenyl)-1-methyl-1H-pyrrole-2-carbonitrile using 2-methyl-acryloyl chloride (53 μL, 0.55 mmol) to provide N-[4-(5-cyano-1-methyl-1H-pyrrol-2-yl)phenyl]-2-methylacrylamide (0.037 g).

HPLC purity 99.2% at 210-370 nm, 8.8 min.; 99.1% at 296 nm, 8.8 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{16}H_{15}N_3O+H^+$, 266.12879; found (ESI, [M+H]$^+$), 266.1295.

Example 13

Ethyl[4-(5-cyano-1-methyl-1H-pyrrol-2-yl)phenyl]carbamate

The title compound was prepared according to the general procedure for acylation of 5-(4-aminophenyl)-1-methyl-1H-pyrrole-2-carbonitrile using ethyl chloroformate (53 μL, 0.55 mmol) to provide ethyl[4-(5-cyano-1-methyl-1H-pyrrol-2-yl)phenyl]carbamate (0.026 g).

HPLC purity 100% at 210-370 mn, 9.3 min.; 100% at 288 nm, 9.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{15}H_{15}N_3O_2+H^+$, 270.12370; found (ESI-FTMS, [M+H]$^+$), 270.12391.

Example 14

Isobutyl[4-(5-cyano-1-methyl-1H-pyrrol-2-yl)phenyl]carbamate

The title compound was prepared according to the general procedure for acylation of 5-(4-aminophenyl)-1-methyl-1H-pyrrole-2-carbonitrile using isobutyl chloroformate (72 μL, 0.55 mmol) to provide isobutyl [4-(5-cyano-1-methyl-1H-pyrrol-2-yl)phenyl]carbamate (0.046 g).

HPLC purity 100% at 210-370 nm, 10.2 min.; 100% at 286 nm, 10.2 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{17}H_{19}N_3O_2+H^+$, 298.15500; found (ESI, [M+H]$^+$), 298.1550.

Example 15

N,N'-bis[4-(5-cyano-1-methyl-1H-pyrrol-2-yl)phenyl]urea

The title compound was prepared according to the general procedure for acylation of 5-(4-aminophenyl)-1-methyl-1H-pyrrole-2-carbonitrile using ethyl chloroformate (53 μL, 0.55 mmol) to provide N,N'-bis[4-(5-cyano-1-methyl-1H-pyrrol-2-yl)phenyl]urea (0.006 g).

HPLC purity 100% at 210-370 nm, 10.5 min.; 100% at 304 nm, 10.5 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{25}H_{20}N_6O+H^+$, 421.17713; found (ESI-FTMS, [M+H]$^+$), 421.1775.

Example 16

[4-(5-cyano-1-methyl-1H-pyrrol-2-yl)phenyl]cyanamide

A solution of 1-methylpyrrole-2-carbonitrile (50.0 g, 0.471 mol) and triisopropyl borate (119.5 mL, 0.518 mol, 1.1 eq.) in THF (600 mL) was stirred and cooled to 0° C. LDA (2M in heptane/THF/ethylbenzene, 306 mL, 0.613 mol, 1.3 eq.) was added in a stream, over about 15 minutes. The temperature of the reaction rose to 24° C., and then began to subside to 7° C. The cooling bath was removed and the mixture was stirred for one hour until no starting material (1-methylpyrrole-2-carbonitrile) was detected by thin layer chromatography (TLC, 1/5: EtOAc/hexane). The reaction mixture was poured gradually into HCl (4N, 542 mL) cooled with ice bath. The ice bath was removed, and the mixture stirred at room temperature for one hour. The organic phase was separated, and the water phase extracted with EtOAc (2×300 mL). The combined organic phases was dried over MgSO$_4$, and concentrated on a rotary evaporator at or below 30° C. The crude product (66 g) was mixed with EtOAc (100 mL), cooled with ice-water bath and basified with cold NaOH (2 N, 500 mL) solution. The cooling bath was removed and the mixture was stirred efficiently until most solids had dissolved. The EtOAc phase was then separated, and the aqueous layer extracted with ether (200 mL). The light colored aqueous phase was cooled to 7° C. and acidified with HCl (6N, 180 mL) to pH 2-3. A light pink solid was collected by filtration, washed with water (2×30 mL), dried by suction for an hour then in a vacuum oven at ambient temperature for 17 h to give 41.6 g (59%) of the N-methylpyrrole-2-carbonitrile-5-boronic acid.

A mixture of cyanogen bromide (5.0 g, 47 mmol), and 4-bromoaniline (17.8 g, 103.4 mmol) in diethylether (150 mL) was stirred for 3 days under nitrogen atmosphere. The reaction was filtered, and the filtrate was concentrated in vacuo at room temperature to give 4-bromophenylcyanamide (8.5 g, 92%) as an off white solid.

4-bromophenylcyanamide (0.651 g, 3.34 mmol), tris(dibenzylideneacetone)dipalladium (76 mg, 0.078 mmol), N-methyl-5-cyanopyrroleboronic acid (1.1 g, 7.3 mmol), and potassium fluoride (0.776 g, 13.2 mmol) were placed in a 40 mL vial fitted with a septa. The vial was then filled with a continuous flow of nitrogen and THF (10 mL) was added. tri-Tert-butylphosphine (10 wt % in hexane) (0.486 mL, 0.078 mmol) was added to the mixture and allowed to stir 3 hours at 50° C. until the starting bromide was consumed. The mixture was then diluted with 1/1 hexane/ethylacetate, filtered through a plug of silica gel, the solvent was evaporated and the residue was flash chromatographed using 5/1, 4/1, then 3/2 Hexane/Ethylacetate to give (0.250 g, 33%) of the title compound.

HPLC purity 100% at 210-370 nm, 10 min.; 100% at 290 nm, 10.1 min.; the Xterra™ RP18 instrument, 3.5µ, 150×4.6 mm column, 1.2 mL/min., 85/15-5/95 (Ammon. found (ESI, [M+H]$^+$), 223.0973 HRMS: calcd for $C_{13}H_{10}N_4$+H$^+$, 223.09782; found (ESI, [M+H]$^+$), 223.0973.

Example 17

[4-(5-cyano-1-methyl-1H-pyrrol-2-yl)-2-methylphenyl]cyanamide

A mixture of cyanogen bromide (5.0 g, 47 mmol) and 4-bromo-2-methylaniline (Aldrich Chemical Company) (19.15 g, 103.4 mmol) in diethylether (150 mL) was stirred for 3 days under nitrogen atmosphere. The reaction was filtered, and the filtrate was concentrated in vacuo at room temperature to give 4-bromophenylcyanamide (8.5 g, 92%) as an off white solid. HRMS: calcd for $C_8H_7BrN_2$, 209.97926; found (EI, M$^+$), 209.9788.

(4-bromo-2-methylphenyl)cyanamide (0.698 g, 3.34 mmol), tris(dibenzylideneacetone)dipalladium (76 mg, 0.083 mmol), N-methyl-5-cyanopyrroleboronic acid (1.1 g, 7.3 mmol), and potassium fluoride (0.776 g, 13.2 mmol) were placed in a 40 mL vial fitted with a septa. The vial was then filled with a continuous flow of nitrogen and THF (10 mL) was added with stirring. Then tri-tert-butylphoshine (10 wt % in hexane) (0.486 mL, 0.083 mmol) was added to the mixture and allowed to stir 3 hours. The mixture was then diluted with 1/1 hexane/ethylacetate and filtered through a plug of silica gel, the reaction was concentrated and the residue was flash chromatographed using 4/1 Hexane/THF to give (0.062 g, 7%) of the title compound.

HPLC purity 100% at 210-370 nm, 10 min.; 99.8% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min HRMS: calcd for $C_{14}H_{12}N_4$+H$^+$, 237.11347; found (ESI-FTMS, [M+H]$^+$), 237.1126

Example 18

[4-(5-cyano-1-methyl-1H-pyrrol-2-yl)-2-ethylphenyl]cyanamide

A mixture of cyanogen bromide (5.0 g, 47 mmol) and 4-bromo-2-ethylaniline (20.6 g, 103 mmol) in diethylether (150 mL) was stirred for 3 days under nitrogen atmosphere. The amine hydrobromide was filtered off, and the filtrate was concentrated in vacuo at room temperature and triturated with hexane to give 4-bromophenylcyanamide (2.3 g, 10%) as an off white solid. HRMS: calcd for $C_9H_9BrN_2$+H$^+$, 225.00218; found (ESI-FTMS, [M+H]$^+$), 225.00277.

4-bromo-2-ethylphenylcyanamide (0.125 g, 0.5 mmol), tris(dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added. Tri-tert-butylphosphine (10 wt % in hexane) (0.0486 mL, 0.0252 mmol) was added to the mixture and allowed to stirred until the starting bromide was consumed. The mixture was then diluted with 1/1 hexane/ethylacetate and filtered through a plug of silica gel, the solvent was evaporated and the residue was flash chromatographed using 4/1 Hexane/THF to give (0.030 g, 24%) the title compound.

HPLC purity 100% at 210-370 nm, 10 min.; 99.4% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. HRMS: calcd for $C_{15}H_{14}N_4$+H$^+$, 251.12912; found (ESI-FTMS, [M+H]$^{1+}$), 251.12953.

Example 19

[4-(5-cyano-1-methyl-1H-pyrrol-2-yl)-2-propylphenyl]cyanamide

A mixture of cyanogen bromide (1.89 g, 17.9 mmol), and 2-n-propylaniline (3.87 g, 28.65 mmol) in ether (50 mL) was stirred for 2.5 hours under nitrogen atmosphere. The mixture was poured into water and extracted with diethylether. The solvent was dried over magnesium sulfate and concentrated in vacuo at room temperature to give 2-propylphenylcyanamide (1.2 g, 26%) as an off white solid.

(2-propylphenyl)cyanamide (0.550 g, 3.43 mmol), sodium acetate (0.278 g, 3.4 mmol), and catalytic acetic acid were combined in dichloromethane (25 mL). Bromine (0.17 mL, 3.43 mmol) was added dropwise and allowed to stir 2.5 hours. The mixture was then poured into brine and extracted with diethylether. The solvent was dried over magnesium sulfate and evaporated in vacuo. The solid was triturated with 9/1 Hexane/acetone, filtered, and dried to give 4-bromo2-propylphenylcyanamide (0.200 g, 24%) an off white solid. HRMS: calcd for $C_{10}H_{11}BrN_2$+H$^+$, 239.01783; found (ESI-FTMS, [M+H]$^+$), 239.01782.

4-bromopropylphenylcyanamide (0.125 g, 5 mmol) tris(dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added with stirring. Tri-tert-butylphosphine (0.0486 mL, 0.0252 mmol) was added to the mixture and allowed to stir until the starting bromide was consumed. The mixture was then diluted with 1/1 hexane/ethylacetate and filtered through a plug of silica gel, solvent was evaporated and the residue was flash chromatographed using 4/1 Hexane/THF to give (0.025 g, 18%) of [4-(5-cyano-1-methyl-1H-pyrrol-2-yl)-2-propylphenyl]cyanamide.

HPLC purity 100% at 210-370 nm, 10 min.; 99% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min HRMS: calcd for $C_{16}H_{16}N_4+H^+$, 265.14477; found (ESI-FTMS, [M+H]$^{1+}$), 265.14535.

Example 20

[4-(5-cyano-1-methyl-1H-pyrrol-2-yl)-2-isopropylphenyl]cyanamide

A mixture of cyanogen bromide (1.89 g, 17.9 mmol) and 2-isopropylaniline (3.875 g, 28.65 mmol) in diethylether (25 mL) was stirred for 2.5 hours under nitrogen atmosphere. The aniline hydrobromide was filtered, the diethylether evaporated, and the residue flash chromatographed using 4/1 Hexane/acetone to give (1.85 g, 64%) the title compound. HRMS: calcd for $C_{10}H_{11}BrN_2+H^+$, 183.08927; found (ESI-FTMS, [M+Na]), 183.08928.

(2-isopropylphenyl) cyanamide (0.550 g, 3.43 mmol) and catalytic acetic acid were combined in dichloromethane (20 mL). Bromine (0.17 mL, 3.43 mmol) was added dropwise and allowed to stir 2.5 hours. The mixture was then poured into brine and extracted with diethylether. The solvent was dried over magnesium sulfate and evaporated in vacuo. The residue flash chromatographed using 9/1, then 4/1 Hexane/acetone to give (0.380 g, 47%) as an off white solid. HRMS: calcd for $C_{10}H_{11}BrN_2+H^+$, 239.01783; found (ESI-FTMS, [M+H]$^{1+}$), 239.01844.

4-bromo-2-isopropylphenylcyanamide (0.132 g, 0.5 mmol) tris (dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added with stirring. Then tri-tert-butylphosphine (0.0486 mL, 0.0252 mmol) was added to the mixture and allowed to stir until starting bromide was consumed. The mixture was then diluted with 1/1 hexane/ethylacetate and filtered through a plug of silica gel, solvent evaporated and the residue was flash chromatographed using 4/1 Hexane/THF to give (0.025 g, 18%) [4-(5-cyano-1-methyl-1H-pyrrol-2-yl)-2-isopropylphenyl]cyanamide.

HPLC purity 100% at 210-370 nm, 10 min.; 99.6% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. HRMS: calcd for $C_{16}H_{16}N_4+H^+$, 265.14477; found (ESI, [M+H]$^+$), 265.1467

Example 21

[2-chloro-4-(5-cyano-1-methyl-1H-pyrrol-2-yl)phenyl]cyanamide

A mixture of cyanogen bromide (1.87 g, 15 mmol), and 2-chloroaniline (3.14 mL, 30 mmol) in ether (15 mL) was stirred for 2 days under nitrogen atmosphere. The reaction was filtered, the filtrate evaporated, and the residue flash chromatographed using 95/5 Hexane/acetone to give (0.430 g, 18%) of the title compound.

(2-chlorophenyl) cyanamide (0.400 g, 2.6 mmol), sodium acetate (0.250 g, 3 mmol) and catalytic acetic acid were combined in dichloromethane (25 mL). Bromine (0.130 mL, 2.5 mmol) was added dropwise and allowed to stir 1 hour. The mixture was then poured into brine and extracted with diethylether. The organic layer was dried over magnesium sulfate and evaporated in vacuo. The residue was flash chromatographed using 85/15 to give (0.220 g, 37%) an off white solid.

4-bromo-2-chlorophenylcyanamide (0.114 g, 0.5 mmol), tris (dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added with stirring. Tri-tert-butylphosphine (10 wt % in hexane) (0.0486 mL, 0.0252 mmol) was added to the mixture and allowed to stir until the starting bromide was consumed. The mixture was then diluted with 1/1 hexane/ethylacetate, filtered through a plug of silica gel, the solvent evaporated and the residue was flash chromatographed using 4/1 Hexane/THF to give [2-chloro-4-(5-cyano-1-methyl-1H-pyrrol-2-yl)phenyl]cyanamide (0.015 g, 12%).

HPLC purity 100% at 210-370 nm, 10 min.; 99% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min HRMS: calcd for $C_{13}H_9ClN_4+H^+$, 257.05885; found (ESI-FTMS, [M+H]$^{1+}$), 257.05911.

Example 22

[2-fluoro-4-(5-cyano-1-methyl-1H-pyrrol-2-yl)phenyl]cyanamide

A mixture of cyanogen bromide (1.87 g, 15 mmol) and 2-fluoroaniline (2.88 mL, 30 mmol) in ether (15 mL) was stirred for 2 days under nitrogen. The reaction was filtered, the filtrate evaporated, and the residue flash chromatographed on silica gel using 95/5 Hexane/acetone to give the title compound (1 g, 25%).

(2-fluorophenyl) cyanamide (0.900 g, 6.6 mmol), sodium acetate (0.572 g, 7 mmol) and catalytic acetic acid were combined in dichloromethane (50 mL). Bromine (0.324 mL, 6.3 mmol) was added dropwise and allowed to stir 1 hour. The mixture was then poured into brine and extracted with diethylether. The solvent was dried over magnesium sulfate and evaporated in vacuo. The residue flash chromatographed using 85/15 to give (0.513 g, 36%) an off white solid. HRMS: calcd for $C_7H_4BrFN_2$, 213.95419; found (EI, M$^+$), 213.9533

4-bromo-2-fluorophenylcyanamide (0.106 g, 0.5 mmol), tris(dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added with stirring. Tri-tert-butylphosphine (10 wt % in hexane) (0.0486 mL, 0.0252 mmol) was added to the mixture and allowed to stir until the starting bromide was consumed. The mixture was then diluted with 1/1 hexane/ethylacetate, filtered through a plug of silica gel, the solvent evaporated and the residue was flash chromatographed on silica gel using 4/1 Hexane/THF to give [2-fluoro-4-(5-cyano-1-methyl-1H-pyrrol-2-yl)phenyl]cyanamide (0.015 g, 12%).

HPLC purity 100% at 210-370 nm, 10 min.; 99.6% at 290 nm, 10.1 min.; the Xterra™ RP18 instrument, 3.5µ, 150×4.6 mm column, 1.2 mL/min., 85/15-5/95 (Ammon. Form. Buff.

Ph=3.5/ACN+MeOH) for 10 min., hold 4 min HRMS: calcd for $C_{13}H_9FN_4+H^+$, 241.08840; found (ESI-FTMS, [M+H]$^{1+}$), 241.08852.

Example 23

[4-(5-cyano-1-methyl-1H-pyrrol-2-yl)-2-methoxyphenyl]cyanamide (2-methoxyphenyl) aniline (2.42 g, 12 mmol) and catalytic acetic acid were combined in dichloromethane (20 mL). Bromine (0.17 mL, 3.43 mmol) was added dropwise and the reaction allowed to stir for 2.5 hours. The mixture was then poured into brine and extracted with diethylether. The organic layer was dried over magnesium sulfate, evaporated in vacuo, and used without further purification.

A mixture of cyanogen bromide (0.550 g, 5.19 mmol), and (4-bromo-2-methoxyphenyl) aniline (2.42 g, 12 mmol) in ether (5 mL) was stirred for 3 days under nitrogen atmosphere. The reaction was filtered, the filtrate evaporated, and the residue flash chromatographed on silica gel using 9/1 Hexane/acetone as eluant to give (0.350 g, 30%) of the title compound.

(4-bromo-2-methoxyphenyl) cyanamide (0.113 g, 0.5 mmol) tris(dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added with stirring. Tri-tert-butylphosphine (0.0486 mL, 0.0252 mmol) was added to the mixture and allowed to stir until the starting bromide was consumed. The mixture was then diluted with 1/1 hexane/ethylacetate, filtered through a plug of silica gel, solvent evaporated and the residue was flash chromatographed using 4/1 Hexane/THF to give [4-(5-cyano-1-methyl-1H-pyrrol-2-yl)-2-methoxyphenyl]cyanamide (0.020 g, 16%).

HPLC purity 98.9% at 210-370 nm, 10 min.; 99% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min HRMS: calcd for $C_{14}H_{12}N_4O+H^+$, 253.10839; found (ESI-FTMS, [M+H]$^{1+}$), 253.10866.

Example 24

[4-(5-cyano-1-methyl-1H-pyrrol-2-yl)-3-methoxyphenyl]cyanamide

A mixture of cyanogen bromide (0.550 g, 5.19 mmol) and 4-bromo-3-methoxyaniline (Lancaster Synthesis Inc., P.O. Box 1000, Windham, N.H. 03087-9977) (2.2 g, 11 mmol) in ether/THF (6 mL) was stirred for 3 days under nitrogen atmosphere. The reaction was filtered, the filtrate evaporated, and the residue flash chromatographed on silica gel using 9/1 Hexane/acetone to give (4-bromo-3-methoxyphenyl)cyanamide (0.300 g, 12%). HRMS: calcd for 2 $C_8H_7BrN_2O+H^{+,}$ 452.95562; found (ESI-FT/MS, [2M+H]$^{1+}$), 452.9556.

4-bromo-3-methoxyphenyl)cyanamide (0.113 g, 0.5 mmol) tris (dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added with stirring. Tri-tert-butylphosphine (10 wt % in hexane) (0.0486 mL, 0.0252 mmol) was added to the mixture and allowed to stir until the starting bromide was consumed. The mixture was then diluted with 1/1 hexane/ethylacetate, filtered through a plug of silica gel, solvent evaporated and the residue was flash chromatographed on silica gel using 4/1 Hexane/THF to give [4-(5-cyano-1-methyl-1H-pyrrol-2-yl)-3-methoxyphenyl]cyanamide (0.020 g, 16%).

HPLC purity 97.8% at 210-370 nm, 10 min.; 98.3% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min HRMS: calcd for $C_{14}H_{12}N_4O+H^+$, 253.10839; found (ESI-FTMS, [M+H]$^+$), 253.1087.

Example 25

[4-(5-cyano-1-methyl-1H-pyrrol-2-yl)-3-methyl phenyl]cyanamide

A mixture of cyanogen bromide (0.550 g, 5.19 mmol), and (4-bromo-3-methylaniline (2.04 g, 11 mmol) (Aldrich Chemical Company) in diethyl ether/THF (8 mL) was stirred for 3 days under nitrogen. The reaction was filtered, the filtrate evaporated, and the residue flash chromatographed on silica gel using 9/1 Hexane/acetone to give (4-bromo-3-methylphenyl)cyanamide (0.289 g, 13%). HRMS: calcd for 2 $C_8H_7BrN_2+H^+$, 420.96579; found (ESI-FT/MS, [2M+H]$^+$), 420.966.

(4-bromo-3-methylphenyl)cyanamide (0.104 g, 0.5 mmol) tris (dibenzylideneacetone) dipalladium (11.6 mg, 0.0126 mmol), N-methyl-5-cyanopyrroleboronic acid (0.150 g, 1 mmol), and potassium carbonate (0.276 g, 2 mmol) were placed in a 40 mL vial fitted with a septa. The vial was then filled with a continuous flow of nitrogen and THF (2 mL) was added with stirring. Tri-tert-butylphosphine (10 wt % in hexane) (0.0486 mL, 0.0252 mmol) was added to the mixture and allowed to stir until the starting bromide was consumed. The mixture was then diluted with 1/1 hexane/ethylacetate, filtered through a plug of silica gel, the solvent evaporated and the residue was flash chromatographed on silica gel using 4/1 Hexane/THF to give [4-(5-cyano-1-methyl-1H-pyrrol-2-yl)-3-methylphenyl]cyanamide (0.015 g, 13%).

HPLC purity 99.2% at 210-370 nm, 10 min.; 99.2% at 290 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min HRMS: calcd for $C_{14}H_{12}N_4+H^+$, 237.11347; found (ESI-FTMS, [M+H]$^+$), 237.11358.

Example 26

[4-(5-cyano-1-methyl-1H-pyrrol-2-yl)phenyl]methylcyanamide

Methylphenylaniline (6 mL, 55 mmol) was dissolved in acetonitrile, the mixture cooled to −20° C., and N-bromosuccinimide (9.76 g, 55 mmol) was added. The stirred mixture was allowed to warm to room temperature. After 3 hours, the solvent was removed in vacuo, the residue dissolved in ethylacetate and washed with water, the organic layer was then dried over magnesium sulfate and evaporated in vacuo to afford (4-bromophenyl)methylaniline (11.3 g) which was used without further purification.

A mixture of cyanogen bromide (3.18 g, 30 mmol), and (4-bromophenyl) methyl aniline (11.25 g, 61 mmol) in ether (50 mL) was stirred for 3 days under nitrogen. The mixture was filtered, the filtrate evaporated, and the residue flash chromatographed on silica gel using 9/1 Hexane/acetone to give (4-bromophenyl)methylcyanamide (2 g, 16 %).

(4-bromophenyl)methyl cyanamide (0.100 g, 0.47 mmol) tetrakis(triphenylphosphine)palladium(0) (0.050 g, 0.043 mmol), N-methyl-5-cyanopyrroleboronic acid (0.150 g, 1 mmol), potassium carbonate (0.345 g, 2.5 mmol) and dimethoxyethylether/water 3:1 were placed in a microwave reaction vial fitted with a septa. The vial was then filled with a continuous flow of nitrogen. Using microwave assisted conditions, the mixture was heated to 100° C. for 15 minutes. The mixture was poured into water, extracted with ethyl acetate, the ethylacetate dried over magnesium sulfate, and evaporated in vacuo. The residue was flash chromatographed using 9/1 Hexane/ethylacetate to give [4-(5-cyano-1-methyl-1H-pyrrol-2-yl)phenyl]methylcyanamide (0.030 g, 27%). HPLC purity 100% at 210-370 nm, 10 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. HRMS: calcd for $C_{14}H_{12}N_4+H^+$, 237.11347; found (ESI, $[M+H]^+$), 237.1127.

| Example # | Compound Name | T47D Cell Alkaline Phosphate Assay $IC_{50}$ (nM) |
|---|---|---|
| 1 | 5-(4-aminophenyl)-1-methyl-1H-pyrrole-2-carbonitrile | 108.9 |
| 2 | 5-(4-amino-3-fluorophenyl)-1-methyl-1H-pyrrole-2-carbonitrile | 65.4 |
| 3 | N-[4-(5-cyano-1-methyl-1H-pyrrol-2-yl)phenyl]-2-furamide | 126.4 |
| 4 | N-[4-(5-cyano-1-methyl-1H-pyrrol-2-yl)phenyl]-3-methylbutanamide | 304.3 |
| 5 | N-[4-(5-cyano-1-methyl-1H-pyrrol-2-yl)phenyl]-2-methylpropanamide | 168 |
| 6 | N-[4-(5-cyano-1-methyl-1H-pyrrol-2-yl)phenyl]propanamide | 76.7 |
| 7 | N-[4-(5-cyano-1-methyl-1H-pyrrol-2-yl)phenyl]butanamide | 78.8 |
| 8 | N-[4-(5-cyano-1-methyl-1H-pyrrol-2-yl)phenyl]acetamide | ~300 |
| 9 | N-[4-(5-cyano-1-methyl-1H-pyrrol-2-yl)phenyl]benzamide | 90.5 |
| 10 | N-[4-(5-cyano-1-methyl-1H-pyrrol-2-yl)phenyl]cyclobutanecarboxamide | 83.9 |
| 11 | N-[4-(5-cyano-1-methyl-1H-pyrrol-2-yl)phenyl]cyclohexanecarboxamide | 325 |
| 12 | N-[4-(5-cyano-1-methyl-1H-pyrrol-2-yl)phenyl]-2-methylacrylamide | 97.2 |
| 13 | ethyl[4-(5-cyano-1-methyl-1H-pyrrol-2-yl)phenyl]carbamate | 265.7 |
| 14 | isobutyl[4-(5-cyano-1-methyl-1H-pyrrol-2-yl)phenyl]carbamate | 378 |
| 15 | N,N'-bis[4-(5-cyano-1-methyl-1H-pyrrol-2-yl)phenyl]urea | 642.1 |
| 16 | [4-(5-cyano-1-methyl-1H-pyrrol-2-yl)phenyl]cyanamide | 54.1 |
| 17 | [4-(5-cyano-1-methyl-1H-pyrrol-2-yl)-2-methylphenyl]cyanamide | 67.1 |
| 18 | [4-(5-cyano-1-methyl-1H-pyrrol-2-yl)-2-ethylphenyl]cyanamide | ~300 |
| 19 | [4-(5-cyano-1-methyl-1H-pyrrol-2-yl)-2-propylphenyl]cyanamide | <300 |
| 20 | [4-(5-cyano-1-methyl-1H-pyrrol-2-yl)-2-isopropylphenyl]cyanamide | <300 |
| 21 | [2-chloro-4-(5-cyano-1-methyl-1H-pyrrol-2-yl)phenyl]cyanamide | 897 |
| 22 | [4-(5-cyano-1-methyl-1H-pyrrol-2-yl)-2-fluorophenyl]cyanamide | 669.9 |
| 23 | [4-(5-cyano-1-methyl-1H-pyrrol-2-yl)-2-methoxyphenyl]cyanamide | <300 |

-continued

| Example # | Compound Name | T47D Cell Alkaline Phosphate Assay $IC_{50}$ (nM) |
|---|---|---|
| 24 | [4-(5-cyano-1-methyl-1H-pyrrol-2-yl)-3-methoxyphenyl]cyanamide | 83.9 |
| 25 | [4-(5-cyano-1-methyl-1H-pyrrol-2-yl)-3-methylphenyl]cyanamide | 55 |
| 26 | [4-(5-cyano-1-methyl-1H-pyrrol-2-yl)phenyl]methylcyanamide | 88.2 |

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A compound having the structure of formula I, or a pharmaceutically acceptable salt thereof:

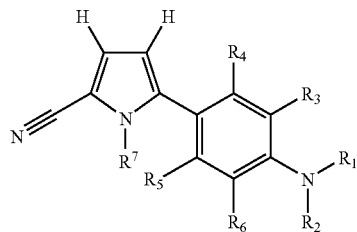

wherein:

$R_1$ is selected from the group consisting of:
H,
CN,
C(O)—$C_1$-$C_6$ alkyl, C(O)—$C_3$-$C_6$ cycloalkyl, C(O)-substituted $C_1$-$C_6$ alkyl, C(O)-aryl, C(O)-substituted aryl, C(O)-heteroaryl, C(O)-heterocycle, C(O)—$C_3$-$C_6$ alkenyl, C(O)—$C_3$-$C_6$ alkynyl, C(O)-substituted $C_3$-$C_6$ alkenyl, C(O)-substituted $C_3$-$C_6$ alkynyl,
C(O)O—$C_1$-$C_6$ alkyl, C(O)O—$C_3$-$C_8$ cycloalkyl, C(O)O-substituted $C_1$-$C_6$ alkyl, C(O)O-aryl, C(O)O-substituted aryl, C(O)O-heteroaryl, C(O)O-heterocycle, C(O)O—$C_3$-$C_6$ alkenyl, C(O)O—$C_3$-$C_6$ alkynyl, C(O)O—$C_3$-$C_6$ substituted alkenyl, C(O)O—$C_3$-$C_6$ substituted alkynyl,
C(O)NH—$C_1$-$C_6$ alkyl, C(O)NH—$C_3$-$C_8$ cycloalkyl, C(O)N-di-$C_3$-$C_8$ cycloalkyl, C(O)N-di $C_1$-$C_6$ alkyl, C(O)N-di-substituted $C_1$-$C_6$ alkyl, C(O)NH-substituted $C_1$-$C_6$ alkyl, C(O)NH-aryl, C(O)N-di-aryl, C(O)NH-substituted aryl, C(O)N-di-substituted aryl, C(O)NH-heteroaryl, C(O)N-di-heteroaryl, C(O)NH-heterocycle, C(O)N-di-heterocycle, C(O)NH—$C_3$-$C_6$ alkenyl, C(O)NH—$C_3$-$C_6$ alkynyl, C(O)NH-substituted $C_3$-$C_6$ alkenyl, and C(O)NH-substituted $C_3$-$C_6$ alkynyl; or $R_1$ is a linking group to a second structure of formula I to form a dimer of formula I, said linking group is a C(O)— group.

$R_2$ is selected from the group consisting of H, $C_1$-$C_6$ alkyl, substituted $C_1$-$C_6$ alkyl, and $C_3$-$C_6$ cycloalkyl;

provided that both $R_1$ and $R_2$ are not H;

provided that where $R_1$ is C(O) substituted aryl, $R_2$ is not H;

provided that when $R_1$ is H and $R_7$ is H, $R_2$ is not $C_1$-$C_6$ alkyl;

$R_3$, $R_4$, $R_5$ and $R_6$ are independently selected from the group consisting of H, halogen, $C_1$-$C_6$ alkyl, substituted $C_1$-$C_6$ alkyl, $C_3$-$C_6$ cycloalkyl, O—$C_1$-$C_6$ alkyl, O—$C_1$-$C_6$ substituted alkyl, aryl, heteroaryl, heterocycle, substituted aryl, substituted heteroaryl, and substituted heterocycle; and $R_7$ is selected from the group consisting of H, $C_1$-$C_6$ alkyl, substituted $C_1$-$C_6$ alkyl, $C_3$-$C_6$ cycloalkyl, and substituted $C_3$-$C_6$ cycloalkyl.

2. The compound according to claim 1, wherein:
$R_1$ is CN;
$R_2$ is H or $C_1$-$C_6$ alkyl;
$R_3$, $R_4$, $R_5$ and $R_6$ are, independently, selected from the group consisting of H, halogen, $C_1$-$C_6$ alkyl, $C_3$-$C_6$ cycloalkyl, O—$C_1$-$C_6$ alkyl, and O—$C_1$-$C_6$ substituted alkyl; and
$R_7$ is H or $C_1$-$C_6$ alkyl.

3. The compound according to claim 1, wherein:
$R_1$ is CN;
$R_2$ is H;
$R_3$, $R_4$, $R_5$ and $R_6$ are, independently, selected from the group consisting of H, halogen, $C_1$-$C_6$ alkyl, and O—$C_1$-$C_6$ alkyl; and
$R_7$ is H or $C_1$-$C_6$ alkyl.

4. The compound according to claim 1, wherein:
$R_1$ is C(O)$C_1$-$C_6$ alkyl, C(O)—$C_3$-$C_5$ cycloalkyl or C(O);
$R_3$, $R_4$, $R_5$ and $R_6$ are, independently, selected from the group consisting H, halogen, $C_1$-$C_6$ alkyl, and O—$C_1$-$C_6$ alkyl; and
$R_7$ is H or $C_1$-$C_6$ alkyl.

5. The compound according to claim 4, wherein:
$R_1$ is C(O)$C_1$-$C_4$ alkyl or C(O)—$C_3$-$C_6$ cycloalkyl;
$R_3$, $R_4$, $R_5$ and $R_6$ are H; and
$R_7$ is $C_1$ alkyl.

6. The compound according to claim 1, wherein:
$R_1$ is selected from the group consisting of CO(NH$_2$), CN, C(O)-heteroaryl, wherein the heteroaryl is a furan, C(O)aryl, wherein the aryl is a phenyl ring, and C(O)O—$C_1$-$C_3$ alkyl.

7. The compound according to claim 1, wherein:
$R_1$ is a C(O) linking group to a second structure of formula (I) to form a dimer thereof.

8. The compound according to claim 1, wherein:
$R_3$ is selected from the group consisting of H, $C_1$-$C_3$ alkyl, a halogen selected from the group consisting of F and Cl, and O—$C_1$-$C_3$ alkyl.

9. The compound according to claim 1, wherein:
$R_4$ is selected from the group consisting of H and O—$C_1$-$C_3$ alkyl.

10. The compound according to claim 1, wherein:
$R_5$ is selected from the group consisting of H, $C_1$-$C_3$ alkyl, a halogen selected from the group consisting of F and Cl, and O—$C_1$-$C_3$ alkyl.

11. The compound according to claim 1, wherein:
$R_6$ is selected from the group consisting of H and halogen, wherein the halogen is F.

12. The compound according to claim 1, wherein:
$R_7$ is $C_1$ alkyl.

13. The compound according to claim 1, wherein the compound is selected from the group consisting of:
N-[4-(5-cyano-1-methyl-1H-pyrrol-2-yl)phenyl]-2-furamide;
N-[4-(5-cyano-1-methyl-1H-pyrrol-2-yl)phenyl]-3-methylbutanamide;
N-[4-(5-cyano-1-methyl-1H-pyrrol-2-yl)phenyl]-2-methylpropanamide;
N-[4-(5-cyano-1-methyl-1H-pyrrol-2-yl)phenyl]propanamide;
N-[4-(5-cyano-1-methyl-1H-pyrrol-2-yl)phenyl]butanamide;
N-[4-(5-cyano-1-methyl-1H-pyrrol-2-yl)phenyl]acetamide;
N-[4-(5-cyano-1-methyl-1H-pyrrol-2-yl)phenyl]benzamide;
N-[4-(5-cyano-1-methyl-1H-pyrrol-2-yl)phenyl]cyclobutanecarboxamide;
N-[4-(5-cyano-1-methyl-1H-pyrrol-2-yl)phenyl]cyclohexanecarboxamide;
N-[4-(5-cyano-1-methyl-1H-pyrrol-2-yl)phenyl]-2-methylacrylamide;
Ethyl[4-(5-cyano-1-methyl-1H-pyrrol-2-yl)phenyl]carbamate;
Isobutyl[4-(5-cyano-1-methyl-1H-pyrrol-2-yl)phenyl]carbamate;
N,N'-bis[4-(5-cyano-1-methyl-1H-pyrrol-2-yl)phenyl]urea;
[4-(5-cyano-1-methyl-1H-pyrrol-2-yl)-2-methylphenyl]cyanamide;
[4-(5-cyano-1-methyl-1H-pyrrol-2-yl)-2-ethylphenyl]cyanamide;
[4-(5-cyano-1-methyl-1H-pyrrol-2-yl)-2-propylphenyl]cyanamide;
[4-(5-cyano-1-methyl-1H-pyrrol-2-yl)-2-isopropylphenyl]cyanamide;
[2-chloro-4-(5-cyano-1-methyl-1H-pyrrol-2-yl)phenyl]cyanamide;
[2-fluoro-4-(5-cyano-1-methyl-1H-pyrrol-2-yl)phenyl]cyanamide;
[4-(5-cyano-1-methyl-1H-pyrrol-2-yl)-2-methoxyphenyl]cyanamide;
[4-(5-cyano-1-methyl-1H-pyrrol-2-yl)-3-methoxyphenyl]cyanamide;
[4-(5-cyano-1-methyl-1H-pyrrol-2-yl)-3-methylphenyl]cyanamide; and
[4-(5-cyano-1-methyl-1H-pyrrol-2-yl)phenyl]methylcyanamide.

14. A pharmaceutical composition comprising a compound according to claim 1 and a pharmaceutically acceptable carrier.

15. The pharmaceutical composition according to claim 14, wherein said composition is an oral dosage unit.

16. The pharmaceutical composition according to claim 14, wherein said composition is a solid oral dosage unit.

17. The pharmaceutical composition according to claim 14, wherein said composition further comprises an estrogen.

18. The pharmaceutical composition according to claim 14, wherein said composition further comprises a progestin.

* * * * *

UNITED STATES PATENT AND TRADEMARK OFFICE
CERTIFICATE OF CORRECTION

| | |
|---|---|
| PATENT NO. | : 7,297,713 B2 |
| APPLICATION NO. | : 11/494069 |
| DATED | : November 20, 2007 |
| INVENTOR(S) | : McComas et al. |

Page 1 of 1

It is certified that error appears in the above-identified patent and that said Letters Patent is hereby corrected as shown below:

(1) On the Title Page Item 56
Page 2, Foreign Patent Documents, add -- WO 95/22520 8/1995 --.

(2) On the Title Page Item 56
Page 2, Foreign Patent Documents, add -- WO 03/091247 11/2003 --.

(3) On the Title Page Item 56
Page 2, Other Publications, add -- LINKER et al., "Substituted N-Aryl Nitrogen Heterocyclic Compounds and Their Use as Herbicides", English Abstract of German Patent No. DE19601626 (July 24, 1997) --.

(4) On the Title Page Item 56
Page 2, Other Publications, add -- LINKER et al., "New Heterocyclic-substituted N-Cyano-Sulfonanilide Compounds, Useful as Total or Selective Pre- or Post- Emergence Herbicides, Showing Dessicant, defoliant, Germination Inhibiting and Especially Weed-Killing Activities", English abstract of German Patent No. DE19918725 (October 26, 2000) --.

(5) Col. 28, line 42, replace "$C(O)-C_3-C_6$" with -- $C(O)-C_3-C_8$ --.

Signed and Sealed this

Thirteenth Day of May, 2008

JON W. DUDAS
*Director of the United States Patent and Trademark Office*